(12) United States Patent
Niven

(10) Patent No.: US 6,848,791 B2
(45) Date of Patent: Feb. 1, 2005

(54) SINGLE-CURVATURE PLACIDO PLATE WITH ADDITIONAL SURFACES

(75) Inventor: Gregg D. Niven, Kaysville, UT (US)

(73) Assignee: Bausch & Lomb Incorporated, Rochester, NY (US)

( * ) Notice: Subject to any disclaimer, the term of this patent is extended or adjusted under 35 U.S.C. 154(b) by 32 days.

(21) Appl. No.: 10/320,839

(22) Filed: Dec. 16, 2002

(65) Prior Publication Data

US 2004/0114108 A1 Jun. 17, 2004

(51) Int. Cl.[7] ................................................. A61B 3/10
(52) U.S. Cl. ...................................................... 351/212
(58) Field of Search ................................. 351/200, 205, 351/211, 212, 221, 246

(56) References Cited

U.S. PATENT DOCUMENTS

| 4,256,385 | A |   | 3/1981 | Cohen et al. ................. 351/13 |
| 5,054,907 | A | * | 10/1991 | Sklar et al. .................. 351/212 |
| 5,841,511 | A |   | 11/1998 | D'Souza et al. ............. 351/212 |
| 5,864,383 | A |   | 1/1999 | Turner et al. ................ 351/212 |
| 6,190,011 | B1 |  | 2/2001 | Fujieda ....................... 351/206 |
| 6,193,371 | B1 | * | 2/2001 | Snook ......................... 351/212 |
| 6,234,632 | B1 | * | 5/2001 | Nakao ......................... 351/212 |
| 6,382,796 | B1 | * | 5/2002 | Ban ............................. 351/212 |
| 2003/0231284 | A1 | * | 12/2003 | Lee et al. ..................... 351/212 |

FOREIGN PATENT DOCUMENTS

GB         2284766 A   *   6/1995    .......... A61F/9/007

* cited by examiner

Primary Examiner—Brian L. Casler
Assistant Examiner—John R Sanders
(74) Attorney, Agent, or Firm—Michael L. Smith

(57) ABSTRACT

A placido device 10 includes a single-curvature, semi-circular screen 12 having an opaque covering which is interrupted along its surface to form an illuminated pattern. A flat top 14 is attached to the top of the screen 12 and angled from the screen front 28 towards the screen bottom 26. Also, a flat bottom 16 is attached to the bottom of the screen 12 and angled from the screen front 28 towards the screen top 24.

11 Claims, 3 Drawing Sheets

SINGLE-CURVATURE PLACIDO PLATE WITH ADDITIONAL SURFACES

BACKGROUND OF THE INVENTION

1. Field of the Invention

The present invention relates generally to corneal topographers and more particularly, to a unique placido plate arrangement.

2. Description of the Related Art

The use of reflected placido rings or patterns to analyze a patient's eye are well-known. Various methods of positioning and illuminating a plurality of placido patterns in front of a patient's cornea have been described in the prior art. Such methods include photokeratoscopes wherein rings are disposed on a plain surface, which is held in front of the patient's cornea and illuminated by a light source to one side of the cornea. Another method is reflecting rings formed on the interior surface of a sphere with the light source outside the sphere, or reflecting rings formed on an inner surface of a cylinder with a light source disposed outside of the cylinder. Yet another method is reflecting rings disposed on the interior surface of a cylindrical cage with the light source disposed within the cage itself.

Illuminating the placido patterns causes reflections of the patterns to appear on the cornea, and these reflections are then depicted, optically or photographically, and then analyzed by an eye specialist. Typically reflected placido rings are circular, and deviations of the cornea from a sphere cause bumps or indentations indicative of irregularities in the cornea, which irregularities will be present in the reflection of the placido patterns. As described in U.S. Pat. No. 5,864,383 to Turner, et al. issued Jan. 26, 1999, the contents of which are incorporated by this reference, sets forth that it is sometimes desirable to change the image or pattern illuminated by an apparatus. For example, a placido ring pattern may be preferred to a checker board pattern or still more preferably, a spider-web pattern as described in co-pending U.S. patent application Ser. No. 10/261,539 may be preferred. As set forth in the patent, changing a pattern on a traditional placido plate was difficult, i.e., on a spherical dish shape placido screen. As taught by Turner, et al., it was an improvement in the art to have an easy to manufacture, non-planer screen, which could be readily associated and disassociated with chosen patterns.

While the invention disclosed by Turner, et al. has proved very successful, it would be desirable to have a placido screen that would provide more surface area coverage of a patient's cornea, while still providing an easily manufactured screen that will easily accommodate a change in placido patterns.

DETAILED DESCRIPTION OF THE DRAWINGS

Figure 1:
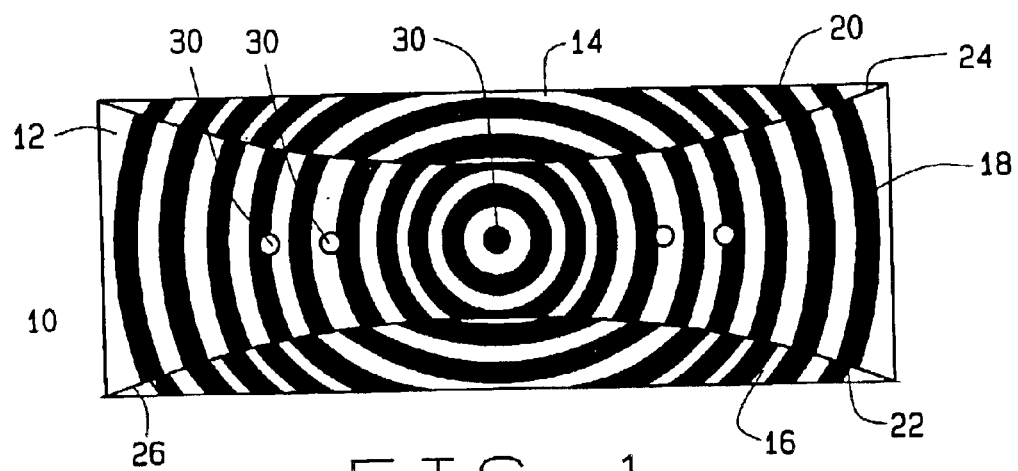
FIG. 1 is a front elevational view of an apparatus in accordance with the present invention.

FIG. 1 shows a placido apparatus 10 in accordance with the present invention.

Figure 3:
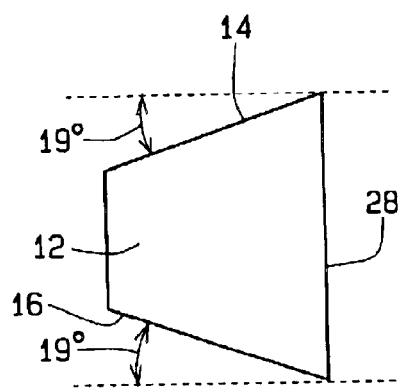
FIG. 3 is a side elevational view of the apparatus of FIG. 1.

The placido apparatus 10 includes a single-curvature, semi-circular screen 12 that is essentially the same as that described in U.S. Pat. No. 5,864,383, the description of which is incorporated herein by reference. The apparatus 10 further includes a flat top 14 and a flat bottom 16. The screen 12 and the flat top and bottom 14 and 16 all include opaque coverings 18, 20, and 22 which are interrupted along the respective surfaces to form an illuminated pattern. The illuminated pattern is accomplished by diffused back lighting as described in U.S. Pat. No. 5,864,383. Screen 12 also includes a top surface 24 and a bottom surface 26 onto which the flat top 14 and flat bottom 16 are attached to the screen by any conventional means. Holes 30 are provided to accommodate fixation lights, illumination lights, or cameras as necessary for obtaining a topography of a patient's cornea. As can be seen from the side view of FIG. 3, flat top 14 and flat bottom 16 are preferably angled from the screen front 28 towards the screen bottom and the screen top respectively. Preferably the angle is approximately 19°. It is believed this amount of tapering of the top and bottom helps create a more regular or even pattern reflected from the cornea compared to a more or less angled top and bottom. If the angle is significantly more or less than 19°, the reflected pattern will appear stretched or compressed.

Preferably the patterns disposed on screen 12 and top and bottom 14 and 16 are detachable from apparatus 10, such that other patterns may be easily placed on apparatus 10 during manufacturing. The other patterns may be those disclosed in U.S. Pat. No. 5,864,383 or the spider-web placido pattern described in co-pending U.S. application Ser. No. 10/261,539 filed on Sep. 30, 2002, entitled "Spider-Web Placido Pattern".

By adding top 14 and bottom 16 to the single-curvature screen 12, it has been found that more information may be found with respect to a patient's cornea over a greater surface area of the cornea. In addition, the top and bottom 14 and 16 also prevent stray light from the examination room from impinging on the cornea. This helps provide a more controlled environment in which to exam a patient's cornea.

Figure 2:
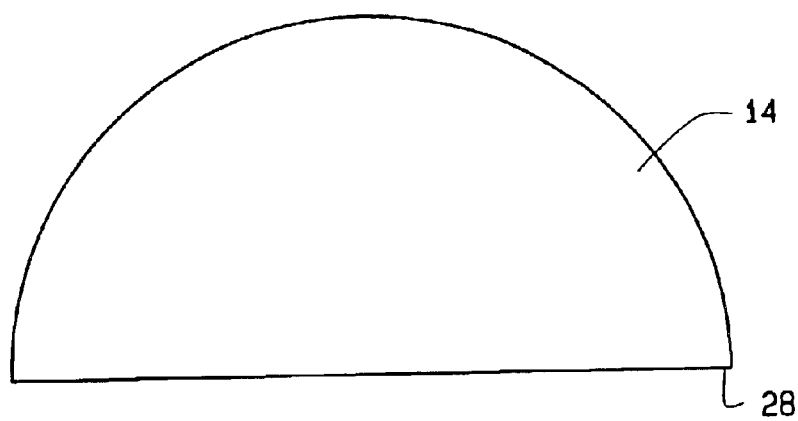
FIG. 2 is a top view of the apparatus of FIG. 1.

FIG. 2 shows a top view of apparatus 10 showing flat top 14 with numeral 28 indicating the front of screen 12.

Figure 4:
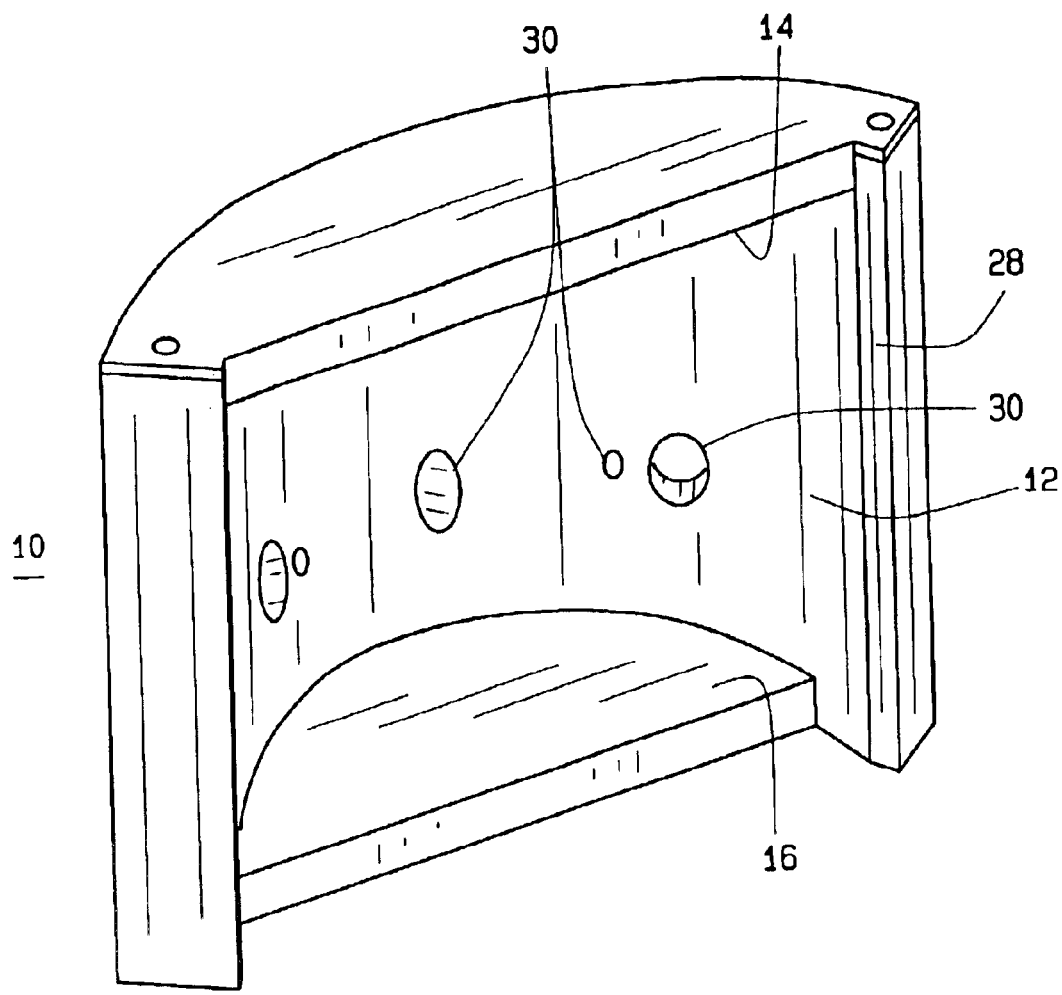
FIG. 4 is a perspective view of a preferred embodiment of the present invention.

FIG. 4 shows a perspective view of placido apparatus 10, including a screen 12, top 14 and bottom 16. You will note that bottom 16 is preferably relieved by approximately ½ inch from the front surface 28. This ½ inch relief of bottom 16 provides clearance for a patient's nose so that a better quality eye exam can be achieved. It is also noted that the placido apparatus 10 of FIG. 4 is shown without the pattern disposed on the apparatus 10.

Figure 5:
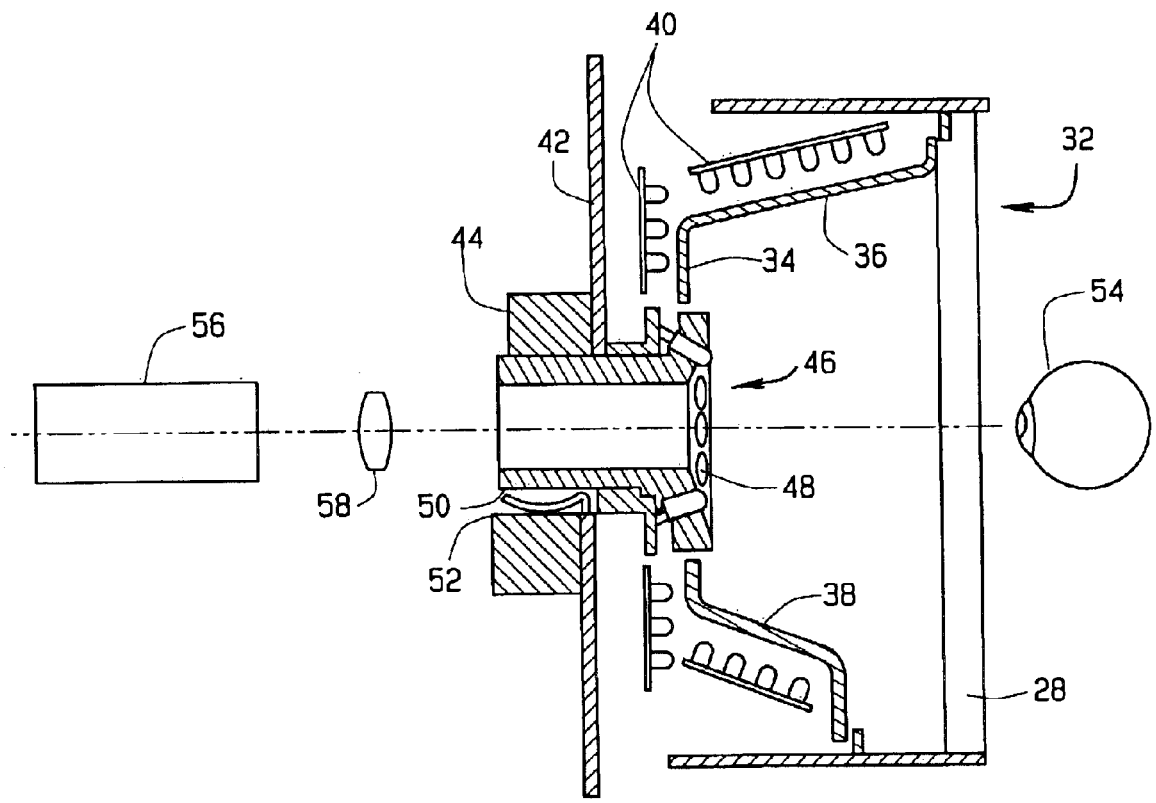
FIG. 5 is a section view of an alternate embodiment of the present invention.

FIG. 5 shows an alternative embodiment of the present invention. A placido apparatus 32 includes a screen 34, a top 36, a bottom 38, essentially the same as those described above. Placido apparatus also includes illumination source 40, which is essentially the same as that described in U.S. Pat. No. 5,864,383. The difference between the invention described above and the U.S. Pat. No. 5,864,383 patent is that the frame 42 has a socket 44 for accommodating removable array light 46.

Removal array 46 preferably is centered within placido apparatus 32 and contains annular ring of light sources 48, which may be incandescent lights, light emitting diodes (LEDs), or infrared light sources depending on the application required by the physician. Removable array 46 is powered through contacts 50 and 52 as shown. In this way, placido apparatus 32 becomes more versatile for the physician, in that difference light arrays may be inserted into the placido apparatus depending on the application required. For instance, if light sources 48 are infrared light sources, an exam of a patient's eye may be accomplished without inducing dilation of eye 54 during the exam. Another alternative (not shown) is a removable array 46 that does not include any light sources but is rather a blank, and therefore, can be used with a disposed pattern as described above. Camera 56 and lens 58 operate in a traditional known manner.

Figure 6:
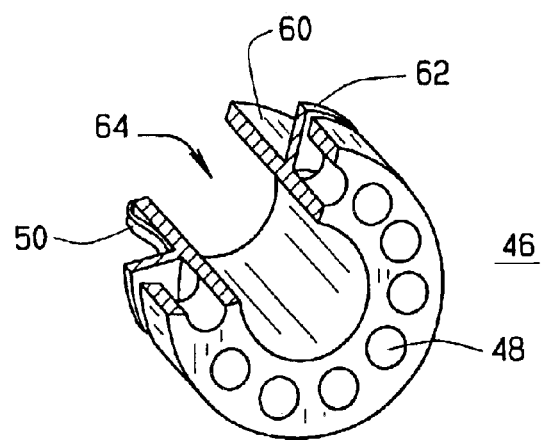
FIG. 6 is a partial perspective view of a portion of FIG. 5

FIG. 6 shows the removable array 46 with light sources 48 contained within housing 60. The light sources 48 are preferably electrically connected to a PC board or other substrate 62 which are then electrically connected to contact 50. Also, preferably removable array 46 includes a cylindrical shaped through-hole 64 for allowing camera 56 to capture a placido image of eye 54.

Thus, there has been shown a new and inventive placido apparatus. Numerous changes in structural details may be made to the preferred embodiment without departing from the scope of the following claims.

I claim:

1. An apparatus for use in analyzing a patient's cornea, the apparatus comprising:
   a single-curvature, semi-circular screen having an opaque covering which is interrupted along its surface to form an illuminated pattern, wherein the screen presents front, top, and bottom surfaces;
   a flat top attached to the top of the screen and angled from the screen front towards the screen bottom;
   a flat bottom attached to the bottom of the screen and angled from the screen front towards the screen top; and
   wherein each of the flat top and flat bottom also has opaque covering interrupted along its surface to form an illuminated pattern.

2. The apparatus of claim 1, wherein the flat top and bottom are each angled at approximately 19° from horizontal.

3. The apparatus of claim 1, wherein the patterns of the screen, the flat top, and the flat bottom are detachable.

4. A placido apparatus for use in analyzing a patient's eye, comprising:
   a placido screen; and
   a removable light array contained within a housing removable connected to the placido screen for providing a desired type of light source for directly illuminating the patient's eye.

5. The invention of claim 4, wherein the removable array further includes an annular light array surrounding a central cylindrical through-hole.

6. The invention of claim 5, wherein the light array is formed of at least one of light emitting diodes (LEDs), infrared light sources, and incandescent light sources.

7. An apparatus for use in analyzing a patient's cornea, the apparatus comprising:
   a single-curvature, semi-circular screen having an opaque covering which is interrupted along its surface to form an illuminated pattern, wherein the screen presents front, top, and bottom surfaces;
   a flat top attached to the top of the screen and angled from the screen front towards the screen bottom;
   a flat bottom attached to the bottom of the screen and angled from the screen front towards the screen top;
   wherein each of the flat top and flat bottom also has opaque covering interrupted along its surface to form an illuminated pattern; and
   a removable light array connected to the screen.

8. The apparatus of claim 7, wherein the flat top and bottom are each angled at approximately 19° from horizontal.

9. The apparatus of claim 7, wherein the patterns of the screen, the flat top, and the flat bottom are detachable.

10. The invention of claim 7, wherein the removable array further includes an annular light array surrounding a central cylindrical through hole.

11. The invention of claim 10, wherein the light array is formed of at least one of light emitting diodes (LEDs), infrared light sources, and incandescent light sources.

* * * * *